United States Patent [19]

Calzi et al.

[11] Patent Number: 4,920,976
[45] Date of Patent: May 1, 1990

[54] SINGLE-USE DEVICES FOR COLLECTING AND HOLDING BLOOD SAMPLES

[75] Inventors: Claudio Calzi, Milan, Italy; Gianfranco Zaccai, Boston, Mass.

[73] Assignee: Instrumentation Laboratory, S.p.A., Milan, Italy

[21] Appl. No.: 282,516

[22] Filed: Dec. 12, 1988

[30] Foreign Application Priority Data

Dec. 18, 1987 [IT] Italy .................... 23092 A/87

[51] Int. Cl.$^5$ .............................. A61B 5/04
[52] U.S. Cl. ................... 128/764; 604/403; 604/415; 215/247
[58] Field of Search ............ 604/403, 415–415; 215/247–249, 363, 355; 188/763, 764, 770

[56] References Cited

U.S. PATENT DOCUMENTS

| 4,133,441 | 1/1979 | Mittleman et al. | 215/247 |
| 4,418,827 | 12/1983 | Butterfield | 215/247 |
| 4,492,634 | 1/1985 | Euclid et al. | 215/247 |
| 4,592,092 | 5/1986 | McPhee | 604/415 |
| 4,682,703 | 7/1987 | Kasai et al. | 215/247 |

Primary Examiner—Stephen C. Pellegrino
Attorney, Agent, or Firm—Alan M. Doernberg

[57] ABSTRACT

In a single-use device for collecting and holding blood samples, provision is made for an evacuated tube with a closure (stopper) that can be pierced by the tip of a needle, the other tip of which is intended to be inserted into a vein of a patient. Disposed below the said pierceable stopper, and in the tube, is a diaphragm intended to passed through by the needle-tip that pierces the stopper, so as to form a supplementar barrier between the interior of the tube and the environment when the pierceable stopper is removed.

9 Claims, 1 Drawing Sheet

SINGLE-USE DEVICES FOR COLLECTING AND HOLDING BLOOD SAMPLES

Various systems are known and used for collecting blood samples intended in particular for subsequent clinical chemistry tests and analyses. The most elementary and conventional of such systems provides for collecting venous blood with a standard syringe and then transferring it to a test tube or other suitable container.

The desirability of preventing contamination of the sample by the environment, and also of the operator by the sample, has led to the development of system that aim to eliminate such possible contaminations.

A known system, designed for reduced operator risk is the evacuated collection tube. This consists of a glass or plastic tube closed at one end and provided at its mouth with a hermetic rubber closure. A high vacuum (long-lasting in time) is created within the tube and, if required, small amounts of chemical substances are placed in the tube, these being adapted to act in the desired manner on the blood sample, for example to prevent blood coagulation or to accelerate the process of separation of the serum from cellular components.

The evacuated tube is used in combination with a 2-tip hypodermic needle: one tip is used for effecting venipuncture in the patient, and the other is inserted into the stopper of the evacuated tube, piercing it and thus allowing blood to flow into the tube.

When the blood sample has been collected and after withdrawing the needle from vein and stopper, the biological sample is contained in the tube in a condition that can be defined as "safe" for the people who are to transport it, centrifuge it, etc., given the substantially hermetic nature of the pack.

This system appears wholly satisfactory as regards collection of the blood sample and handling of the stoppered container, but its limitations are apparent when the operator has to remove the rubber stopper to be able to have access to the sample contained in the tube. The removal of the stopper is, for example, requisite when the tube is placed in an automated or semi-automated machine for aspirating, by means of a tube, measured amounts of blood to be analysed.

For, without the stopper, the open mouth of the tube has dimensions equal to its diameter and any handling error causes the content to escape and thus exposes the operator to the risk of contagion or infection.

The present invention proposes to obviate the problem described above, from which the blood collection system using an evacuated tube and pierceable cap suffer, by substantially limiting the possibility of contamination of the environment by the sample and, to a certain degree, also the same contamination in reverse, even if the operator handles the sample container without special care and attention or if, accidentally, he handles it improperly.

SUMMARY OF THE INVENTION

For such purpose the invention provides a single-use device for collecting and containing blood samples, comprising a rigid tube closed at one end and having at the other end a hermetic stopper wich can be pierced by the first tip of a needle, the second tip of which is adapted to be used for venipuncture, wherein inside the said tube, at a limited distance from the stopper, there is disposed in a stable position and so as to set up a seal with the inner wall of the tube a low thickness diaphragm, the first tip of the needle being adapted to pass through the diaphragm, after piercing the stopper.

The characteristics of the invention, and its advantages over the known art, will become more apparent from the following description of exemplary embodiments of the invention, referred to the appended drawings, in which.

DETAILED DESCRIPTION

Figure 1:
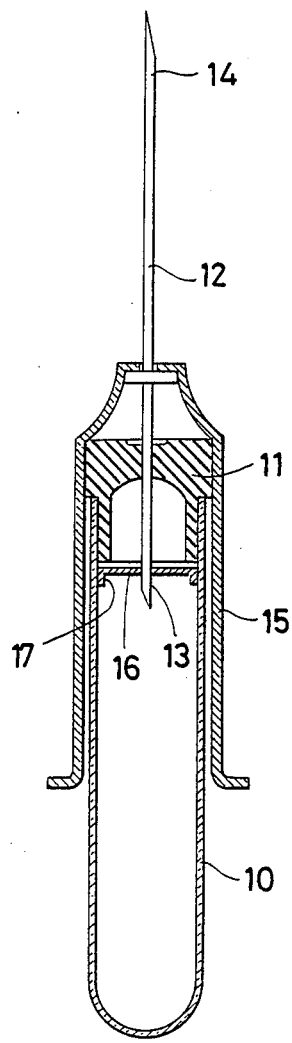
FIG. 1 is a general longitudinal section view of a device according to a first embodiment of the invention.

With reference to FIG. 1, a device for the collection and containment of a blood sample is shown consisting of a test tube 10 closed by a stopper 11 made of rubber or elastomer or other suitable material. The stopper 11 must be able to be fitted into the mouth of the test tube 10 so as to provide a substantially hermetic seal therewith, and it must be pierceable by one of the tips of the needle 12, such tip being indicated by the numeral 13. The other tip 14 of the needle 12 must be suitable for venipuncture, by the usual technique used for collecting blood samples. FIG. 1 also illustrates a grip portion 15 able to slide on the outer wall of the tube 10 to guide the needle 12, which is fixed on it, correctly to pierce the stopper 11, as well as serving as a grip for the purpose of venipuncture.

What has thus far been described is well known to persons with ordinary skill in the art, as is also the manner of operating the device. Briefly, the tube 10 is closed by its stopper 11 in conditions of considerably high vacuum. As a result of the hermetic nature of the whole, the vacuum persists for a reasonable long period of time, on the order of years. Separately from the tube 10, the needle 12 is used for the venipuncture; thereafter, the container 10 is brought close to the tip 13 of the needle which is pressed to pass through the stopper 11, so that the device overall comes to take on the configuration shown in FIG. 1. The vacuum in the tube 10 allows the desired amount of blood to flow into it. It should incidentally be noted that the tip 13 of the needle can carry a provisional protector, rupturable by the insertion of the said tip into the stopper 11 in order to prevent escape of blood from the tip 13 before it pierces the stopper 11.

In accordance with the invention, below the stopper 11 there is force-fitted in the tube-shaped container 10 a thin diaphragm 16. If, as a result of its low thickness, this diaphragm has low resistance to lateral distortion, it will advantageously feature a perimetric reinforcement border 17, more or less diametrically extended, that will provide the required resistance to a forced fitting against the inner wall of the tube 10 sufficing to obtain a satisfactory seal—which the object of the invention calls for—and a satisfactory positional stability of the diaphragm. The diaphragm should not be displaced by the usual stresses to which the tube is subject, in particular by its centrifugation. The longitudinal position of the diaphragm 16 inside the tube 10 should be at a minimal distance from the stopper 11, one reason for this being to prevent any substantial reduction of the useful volume of the tube. The tip 13 of the needle should be sufficiently long to pass through the diaphragm 16 after piercing the stopper 11.

It will be apparent that, by adopting the device fitted with the diaphragm 16 in accordance with the invention, after removable of the stopper 11 the tube 10 will remain closed by the diaphragm 16 itself; although the diaphragm 16 may have at its centre a small perforation caused by the needle 12 that passes through it, it will in any case effectively prevent any escape of the blood contained in the tube 10 if the tube 10 is handled without due care and attention.

In these conditions of content-safety the tube 10 can be handled without any substantial risk of escape or leakage and be placed in the blood sample treatment apparatus.

The small thickness of the diaphragm permits it to be passed through by the needles used in automated or semi-automated apparatus for quantitatively withdrawing volumes of blood to be sent for analysis.

The configuration of the stopper 11 can be modified with respect to the conventional configuration of such stoppers so as better to adapt to the diaphragm provided for by the invention.

Figure 2:
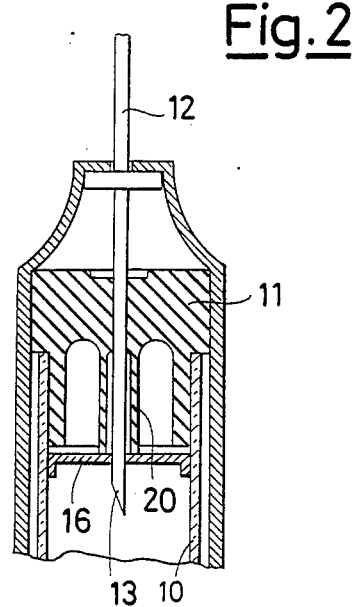
FIG. 2 is a partial view similar to FIG. 1, illustrating a second embodiment.

FIG. 2 of the drawings shows the stopper 11 embodied with an internal extension 20 which defines a channel-shaped structure which projects very close to, or even so as to be in contact with, the diaphragm 16.

The space between the stopper 11 and the diaphragm 16 is in this way substantially reduced and, in addition, needle-alignment is improved in that the tip 13 of the needle is guided by the extension 20 towards the centre of the diaphragm. This can be of particular advantage when needle-alignment is not assured by some other guide element of the type illustrated in FIG. 1 having the form of a grip 15.

Figure 3:
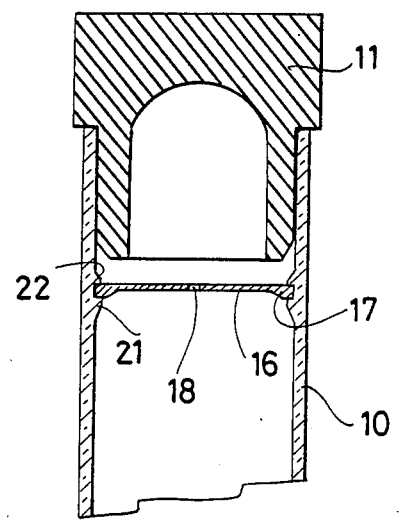
FIG. 3 is a partial view of a hermetic container forming part of the device according to the invention, in a third embodiment.

A correct positioning of the diaphragm 16 inside the tube 10 can be made easier by forming a seat proximally to the inner wall of the tube 10. FIG. 3 of the drawings shows two annular projections 21 and 22 formed on the inner wall of the tube 10, between which the peripheral border 17 of the diaphragm 16 is inserted. A correct positioning can of course also be obtained by means of any kind of annular seat into which the border 17 of the diaphragm 16 can be placed, and here firmly locked, so as not to be displaced by the usual stresses, for example a tube centrifugation. In particular, FIG. 3 shows the diaphragm 16 featuring a small pre-formed perforation 18 at its centre. This perforation, which can be adopted whatever the specific configuration of the device according to the invention, can serve to prevent pressure differences from occuring between the area of the tube below the diaphragm 16 for the purpose of holding the blood sample and the area of the tube between the diaphragm 16 and stopper 11.

The communication represented by the perforation 18 prevents, for example, the possibility of transient pressure differences between the aforesaid two areas of the tube when the stopper 11 is removed, since in this event the latter acts in the same way as a piston, below which a transient pressure depression occurs on rising.

The perforation 18 makes it easier for the tip 13 of the needle to pass through the diaphragm 16, thus limiting the risk of uncontrolled tearing of the latter. In addition, this perforation 18 will also make it easier for the acicular (needlelike) narrow-gauge tubes—used in analytical apparatus for quantitatively withdrawing blood from the tube for analysis purposes—to pass into the interior of the tube 10.

To fulfil its function advantageously the perforation 18 can be of considerably small diameter, for example of the order of half a millimetre. The existence of the perforation 18 does not, therefore, substantially jeopardize the safety of the container, after removal of the stopper 11, against reciprocal contamination of sample and environment.

It is noteworthy that, as well as making its handling much safer and thus greatly reducing the risk of accidental spilling or escape of the biological fluid, the diaphragm 16 placed within the tube 10 in accordance with the invention protects the said fluid from any contamination by the environment. The possibility of such contamination is therefore very much reduced and interactions with the ambience such as, typically, evaporation of the water contained in the biological fluid when the tube 10 awaits, after removal of the stopper 11, withdrawal from it of the amount of sample to be sent for analysis, is prevented or substantially retarded. Such evaporation may be fairly appreciable when the tube 10 is maintained at a not low temperature in a controlled-temperature environment.

Some exemplifying forms of practical embodiment incorporating the innovative principles of the invention have heretofore been described; it will however be clear that persons skilled in the art may introduce further variants of embodiment without going beyond the scope of the present invention.

We claim:

1. Single-use device for collecting and containing blood samples, comprising a rigid tube closed at one end and having at the other end an airtight stopper which can be pierced by the first tip of a needle, the second tip of which is adapted to be used for venipuncture, wherein within the tube, at a limited distance from the stopper there is disposed in a stable position and forming a seal with the inner wall of the tube a low-thickness diaphragm, the first tip of the needle being adapted to pass through the diaphragm after piercing the stopper.

2. Device as described in claim 1, wherein the diaphragm has a peripheral thickened portion engaged against the inner wall of the tube.

3. Device as described in claim 1, wherein the diaphragm has at its centre a small preformed perforation, to place the areas of the tube divided by the said diaphragm into communication.

4. Device as described in claim 1, wherein the stopper, proximally to the area intended to be pierced by the needle, forms a channel-shaped extension terminating adjacent close to the central portion of the diaphragm.

5. Device as described in claim 1 wherein securing means are provided to prevent the diaphragm from sliding in the tube.

6. Device as described in claim 5 wherein the securing means comprises a diaphragm border forced by friction against the inner wall of the tube.

7. Device as described in claim 1 wherein the diaphragm forms a thickened portion at its periphery and wherein the thickened portion of the diaphragm is received within the annular seat.

8. Device as claimed in claim 1 wherein the diaphragm forms a thickened portion at its periphery.

9. Single-use device for collecting and containing blood samples, comprising a rigid tube closed at one end and having at the other end an airtight stopper which can be pierced by the first tip of a needle, the second tip of which is adapted to be used for venipuncture, wherein within the tube, at a limited distance from the stopper there is disposed in a stable position and forming a seal with the inner wall of the tube a low-thickness diaphragm, the first tip of the needle being adapted to pass through the diaphragm after piercing the stopper, the device further comprising securing means for preventing the diaphragm from sliding in the tube, the securing means including an annular seat formed on the interior wall of the tube, a peripheral portion of the diaphragm being received within the annular seat.

* * * * *

UNITED STATES PATENT AND TRADEMARK OFFICE
CERTIFICATE OF CORRECTION

PATENT NO. :   4,920,976
DATED       :   May 1, 1990
INVENTOR(S) :   Claudio Calzi and Gianfranco Zaccai It is certified that error appears in the above-identified patent and that said Letters Patent is hereby corrected as shown below:

On the cover, under "References Cited", add:

-- 2,457,120    12/1948      Brandon
   3,659,587     5/1972      Baldwin
   3,771,965    11/1973      Grams
            FOREIGN PATENT DOCUMENTS
   1,557,037     7/1967      Germany
            OTHER REFERENCES
   Becton Dickinson and Company, "VACUTAINER Brand
   Evacuated Blood Culture Tube" (12/1986)    --

Abstract, line 6, after "intended to" insert -- be --

Col. 4, lines 61-62, delete claim 8

Col. 4, line 63, change "9" to -- 8 --

Col. 6, after line 4, insert:

-- 9. Device as claimed in claim 8 wherein the
   diaphragm forms a thickened portion at its
   periphery.              --

Signed and Sealed this

Twentieth Day of August, 1991

Attest:

HARRY F. MANBECK, JR.

*Attesting Officer*           *Commissioner of Patents and Trademarks*